United States Patent [19]

Ross

[11] Patent Number: 5,019,079

[45] Date of Patent: May 28, 1991

[54] BONE SCREW

[75] Inventor: Randall D. Ross, Largo, Fla.

[73] Assignee: Zimmer, Inc., Warsaw, Ind.

[21] Appl. No.: 438,879

[22] Filed: Nov. 20, 1989

[51] Int. Cl.[5] .......................... A61F 5/04; F16B 35/00
[52] U.S. Cl. ...................................... 606/72; 606/73; 411/389
[58] Field of Search .................. 606/65, 72, 73, 66, 606/67, 68, 59; 411/383, 384, 389, 395

[56] References Cited

U.S. PATENT DOCUMENTS

| | | | |
|---|---|---|---|
| 1,789,060 | 1/1931 | Weisenbach | 606/73 |
| 2,382,019 | 8/1945 | Miller | 606/72 |
| 2,489,870 | 11/1949 | Ozus | 606/73 |
| 2,570,465 | 10/1951 | Lundholm | 606/65 |
| 2,801,631 | 8/1957 | Charnley | 606/65 |
| 4,175,555 | 11/1979 | Herbert | 606/73 |
| 4,456,005 | 6/1984 | Lichty | 606/73 |
| 4,463,753 | 8/1984 | Gustilo | 606/73 |
| 4,537,185 | 8/1985 | Stednitz | 606/73 |
| 4,640,271 | 2/1987 | Lower | 606/73 |
| 4,648,388 | 3/1987 | Steffee | 606/73 |
| 4,723,541 | 2/1988 | Reese | 606/73 |
| 4,858,601 | 8/1989 | Glisson | 411/389 |

*Primary Examiner*—Robert A. Hafer
*Assistant Examiner*—Michael Brown
*Attorney, Agent, or Firm*—Epstein, Edell & Retzer

[57] ABSTRACT

A guided bone screw includes proximal and distal sections threaded with different pitches in the same direction and spaced by an unthreaded intermediate section having a shorter length than the distal section with a diameter substantially equal to the major diameter of the distal section. The intermediate section diameter is greater than the minor diameter and smaller than the major diameter of the proximal section thread. The threads of both the distal and proximal sections are self-tapping. A guide bore for a guide wire extends the entire length of the screw. Two drive recesses are disposed in the proximal screw end on opposite sides of the guide bore for engagement by a two-pin screwdriver. The unthreaded intermediate section radially fills the bone bore in which it is implanted to provide lateral stability for the bone screw.

18 Claims, 1 Drawing Sheet

U.S. Patent   May 28, 1991   5,019,079
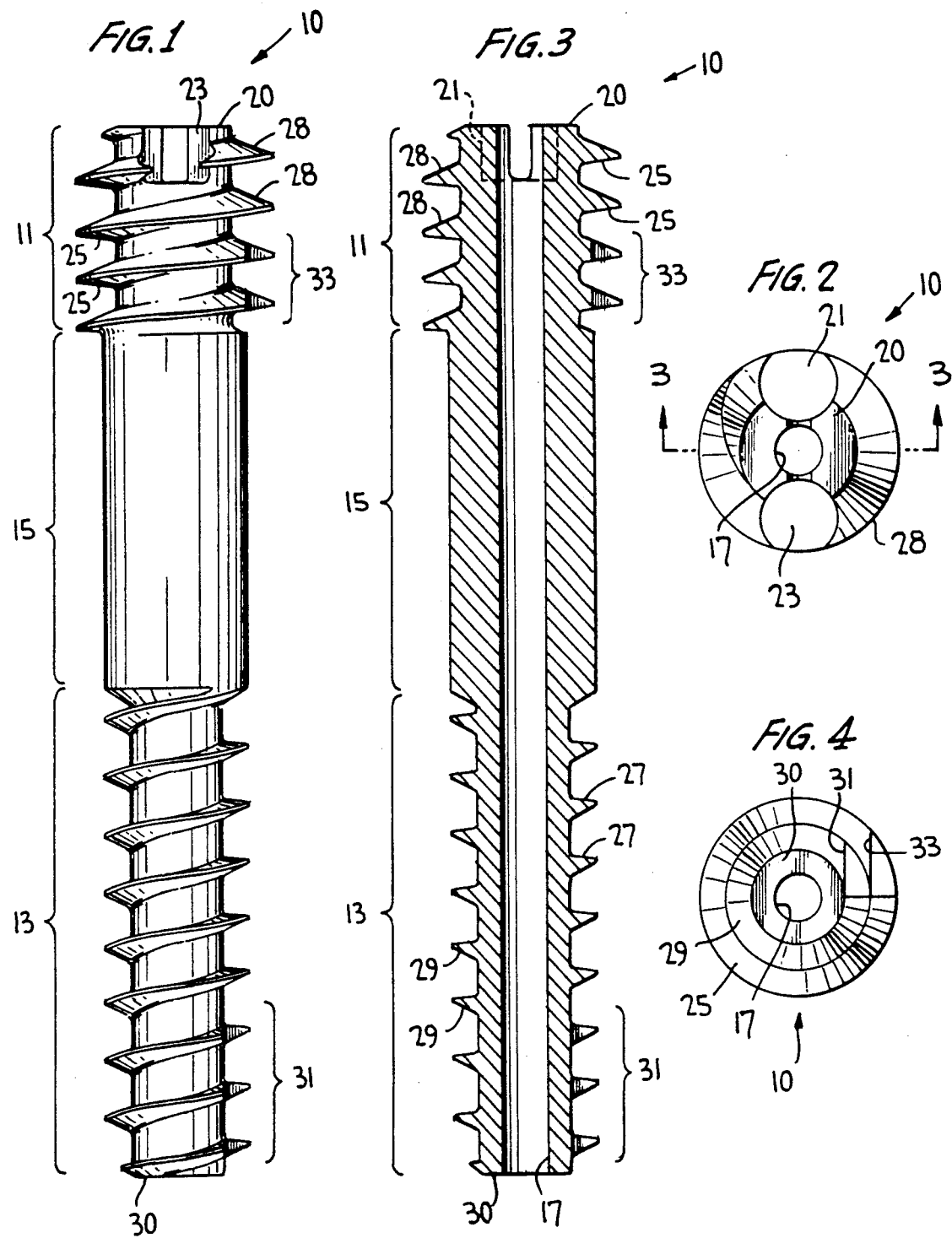

0
BONE SCREW

BACKGROUND OF THE INVENTION

1. Technical Field:

The present invention relates to bone screws and, more particularly, to improvements in guided bone screws whereby safe insertion is facilitated and stability is enhanced.

2. Discussion of the Prior Art:

A prior art bone screw disclosed in U.S. Pat. No. 4,175,555 (Herbert) has like-handed thread at its distal and proximal ends separated by an unthreaded intermediate section. To function as a compression screw the proximal end thread pitch is less than the distal end thread pitch. Thus, when the screw is advanced in pretapped bores through two severed bone fragments being joined, the large pitch distal end of the screw advances a greater distance in the remote bone fragment, per screw turn, than the distance advanced by the proximal end of the screw in the near bone fragment. The result is a compression of the bone fragments at the fragment interface.

The Herbert bone screw described above has certain drawbacks that affect its practical utilization. For example, the diameter of the unthreaded intermediate section is smaller than the major diameter of the threaded distal end, and smaller than the minor diameter of the threaded proximal end. As a consequence, the unthreaded intermediate section resides in a bore section that must be large enough to accommodate the minor diameter of the proximal end thread and, therefore, does not fill the bore. The result is a lateral instability that sacrifices the integrity of the fragment interface during the healing process.

The unthreaded intermediate section of the Herbert bone screw is also required to be axially longer than each of the threaded end segments. The stated reason for this requirement is to assure that there is no thread at the fragment interface. While it is necessary to avoid thread at the fragment interface, the elongation of the intermediate screw section in the Herbert screw results in axially short threaded sections (i.e., fewer turns) and, consequently, less available compressive forces at the interface.

In addition, the unthreaded intermediate section of the Herbert bone screw is required to have a diameter that is smaller than both the major and minor diameters of the proximal end thread. This adds to the lateral instability described above. More specifically, the pretapped bore in the proximal bore section must be diametrically wider than the smaller diameter intermediate section. As a result, the portion of the intermediate section residing in that bore does not fill the bore.

OBJECTS AND SUMMARY OF THE INVENTION

It is therefore an object of the present invention to provide a bone screw in which the disadvantageous features noted above are avoided.

It is another object of the present to provide a bone screw configured to remain laterally stable when implanted.

A further object of the present invention is to provide a bone screw that is capable of exerting increased compression forces, as compared to prior art bone screws, without increasing the length or width of the screw.

In accordance with the present invention a bone screw has self-tapping proximal and distal threaded sections separated by an intermediate unthreaded section. The distal threaded section is longer than the intermediate section to provide additional gripping threads on the screw. The diameter of the intermediate section is substantially the same as the major diameter of the distal threaded section to permit the intermediate section to fill the section of the bone bore overlapping both the near and remote bone fragments for improved lateral stability. The intermediate section diameter is also larger than the minor diameter of the proximal threaded section to permit the intermediate section to fill the bore section residing only in the proximal or near bone fragment for additional lateral stability. The self-tapping threads at the proximal and distal sections eliminate the need for a separate bore-tapping step by the surgeon as part of the screw implantation procedure.

The bone screw is cannulated for use with a guide wire in a well-known manner. Two recessed drive bores at the proximal end of the screw are adapted to receive a two-pin drive device for easily controlled insertion of the screw. The thread on both the distal and proximal ends is provided with a substantially flat radial surface facing the bone fragment interface to maximize the thread surface area through which the compressive forces are applied to the bone fragments.

BRIEF DESCRIPTION OF THE DRAWINGS

These and other objects, features and many of the attendant advantages of the present invention will be appreciated more readily as they become better understood from a reading of the following description considered in connection with the accompanying drawings wherein like parts in each of the several figures are identified by the same reference characters, and wherein:

FIG. 1 is side view in elevation of a bone screw constructed in accordance with the present invention;

FIG. 2 is a top view in plan of the bone screw of FIG. 1;

FIG. 3 is a view in longitudinal section taking along lines 3—3 of FIG. 2; and

FIG. 4 is a bottom view in plan of the bone screw of FIG. 1.

DESCRIPTION OF THE PREFERRED EMBODIMENT

Referring to the drawings in greater detail, a bone screw 10 of the present invention includes a threaded longitudinal section 11 terminating at proximal end 20, a threaded longitudinal section 13 terminating at distal end 30, and an unthreaded cylindrical intermediate end section or shank 15 extending between the two threaded sections 11 and 13. A guide bore 17 is defined entirely through screw 10 along its central longitudinal axis between proximal end 20 and distal end 30. The proximal end 20 has two generally cylindrical and similarly configured recesses 21, 23 defined therein so as to extend a short longitudinal distance on diametrically opposite sides of guide bore 17. Recesses 21, 23 serve to receive cylindrical pins of a drive tool (not shown) that may be rotated to drive the screw into a bore defined through two bone fragments at a fracture site. The diameter of recesses 21, 23 in the illustrated embodiment is sufficiently large that the recesses extend radially beyond the flat end surface 20 and into the initial threads of proximal threaded section 11.

The threads of sections 11 and 13 are like-handed; that is, they extend in the same angular direction about the screw. The pitch of the threaded distal end section 13 is slightly greater than the pitch of the threaded proximal end section 11. Accordingly, when the screw is rotatably driven into a bone bore, the distal end section 13 tends to advance a small amount further than the proximal end section 11 with each rotation of the screw. This creates tensional forces in the screw which, in turn, applies compression forces to the bone fragments in the direction toward the fragment interface. To more efficiently apply these forces, the threads of the two sections 11 and 13 are asymmetrical about their crests with each thread having a respective surface 25, 27 extending substantially radially (i.e., normal to the longitudinal axis of the screw when viewed in any plane containing that axis) so as to face intermediate section 15. The radial surfaces 25, 27 efficiently and uniformly distribute the compressive forces to the surrounding bone tissue in a direction parallel to the longitudinal dimension of the screw. The opposite respective surfaces 28, 29 of the thread are relatively acute to the screw axis and face in opposite directions generally toward proximal end 20 and distal end 30, respectively, of the screw.

For reasons that are described in detail below, the various sections of screw 10 have important relative dimensions. First, the diameter of intermediate section 15 is substantially the same as the major diameter (i.e., the diameter of the crest) of the threads in distal threaded section 13. Second, the length of distal threaded section 13 is somewhat greater than the length of the shank or the intermediate section 15. Further, the diameter of intermediate section 15 is greater than the minor diameter (i.e., the diameter at the root) of the threads in proximal end section 11.

In addition to the relative dimensions described above, the bone screw of the present invention is characterized by self-tapping threads on both the distal section 13 and the proximal end section 11. The self-tapping feature eliminates the need for a separate tapping procedure as part of the screw implantation process. More specifically, the first few lengths of thread of distal section 13 are provided with a flute 31 configured to present a cutting edge that is radial to the screw. A similar flute 33 is provided in the first few lengths of thread in the proximal end section 11.

The bone screw of the present invention is typically employed to repair fractures of small bones, such as acute fractures of the volar (i.e., wrist) scaphoid bone. In order to employ bone screw 10, it is first necessary to drill bores through the bone fragments. A narrow bone bore, of diameter approximately equal to the minor diameter of distal threaded section 13, is drilled through the near bone fragment, past the fragment interface, and into the far bone fragment to a depth at least long enough to accommodate the entire length of threaded distal section 13. A wider bone bore, disposed concentrically with the narrow bore, is drilled through the near bone fragment and a short distance past the fragment interface into the far bone fragment. The wide bore has a diameter approximately equal to the diameter of the intermediate section 15. The two bores may be formed as a part of a single step using a stepped drill. A guide wire is inserted through the narrow and wide bone bores, either as part of the drilling process or afterward. Screw 10 is inserted onto the guide wire via guide bore 17 to properly position distal end 30 of the screw at the base of wide bone bore and the entrance to the narrow bone bore. Then, with the use of an appropriate two-pin driving tool engaging drive bores 21, 23, the bone screw is driven into the bone bores. The self-tapping feature provided by flutes 31, 33 in sections 13, 11, respectively, causes appropriate threads to be formed in the bone bores to engage the threaded screw sections. As defined above, the self-tapping features of both threaded sections 11 and 13 avoids the need for the surgeon to employ a self-tapping procedure after the bone bores are drilled.

Bone screw 10 is preferably inserted into the fracture site until the proximal end 20 is flush with or recessed below the exposed surface of the near bone fragment, thereby eliminating any protrusion of the screw from the bone that might otherwise interfere with normal use of the joint. When the screw is thusly inserted, intermediate section 15 extends between the two bone fragments across the fragment interface. The forward end of the intermediate section extends slightly into the distal or narrow bone bore as threaded by the self-tapping section 31 of the thread on distal section 13. The remainder of intermediate section 15 resides in the wider or proximal bone bore having substantially the same diameter as intermediate section 15. Accordingly, intermediate section 15 completely fills these bone bore portions and thereby precludes lateral movement of the screw, particularly at the bone fragment interface.

Threaded distal section 13 is axially longer than intermediate section 15, typically by fifteen to twenty-five percent. In the preferred embodiment of the invention, threaded distal section 13 is between seventeen and eighteen percent longer than intermediate section 15. Therefore, for a screw of given overall length, the bone screw 10 of the present invention provides more thread in distal section 13, and hence a greater surface area 27, than for a screw wherein the unthreaded intermediate section is required to be longer than the distal threaded section.

Although bone screw 10 can be fabricated from a variety of materials, the preferred material is titanium which has negligible susceptibility to corrosion and exhibits excellent biocompatibility.

In the preferred embodiment of bone screw 10, the facing thread surfaces 25, 27 that apply the compressive forces to the bone fragments are disposed at an angle 5° or less to normal or radial from the screw axis. The acute thread surfaces 28, 29 are typically at angles of 20° and 25°, respectively, to normal. The pitch of the thread along distal section 13 is 0.047 inch, and along proximal section 11 is 0.043 inch. The thread at proximal section 11 has a major diameter of 0.157 inch and the minor diameter of 0.094 inch; the thread at distal section 13 has a major diameter of 0.118 inch and a minor diameter of 0.075 inch. The diameter of intermediate section 15 is 0.118 inch. Bone screw 10 can be made in different lengths to compress different size fractures for different size bones. In one embodiment, wherein the bone screw is 0.630 inch in length, distal threaded section 13 is 0.245 inch long, intermediate section 15 is 0.208 inch long, and proximal threaded section 11 is 0.177 inch long. For another embodiment having a total bone screw length of 1.181 inch, distal thread section 13 is 0.542 inch long, intermediate section 15 is 0.462 inch long, and proximal thread section 11 is 0.177 inch long.

The dimensions set forth above are by way of example only for preferred embodiments of the present invention. It is to be understood that the important aspects of the present invention reside in the relative dimensions described herein. In particular, the diameter of intermediate section 15 is equal to the major diameter of the threads of distal section 13, greater than the minor diameter of the threads of proximal section 11, and less than the major diameter of the threads of proximal section 11. In addition, distal threaded section 13 is longer than intermediate section 15. Another important feature of the bone screw of the present invention is the self-tapping nature of threaded sections 11 and 13. Finally, a feature of the invention resides in the two-point drive arrangement wherein two recesses 21, 23 are disposed on opposite sides of guide bore 17 at proximal end 20 in position to be engaged and rotatably driven by a screw driver having a corresponding two-pin drive tip.

From the foregoing description, it will be appreciated that the present invention makes available a novel guided bone screw having improved lateral stability and greater thread surface for a given screw length.

Having described a preferred embodiment of a new and improved bone screw in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A bone screw connecting two pieces of bone comprising:
   a distal end;
   a proximal end;
   a generally cylindrical unthreaded intermediate section having a predetermined diameter;
   a threaded proximal section extending from said proximal end to said intermediate section and having a first uniformly-pitched thread;
   a threaded distal section extending from said distal end to said intermediate section and having a second uniformly-pitched thread that is threaded in the same direction as said first threads;
   wherein the pitch of said second thread is greater than the pitch of said first thread; and
   wherein said second thread has a major diameter substantially equal to said predetermined diameter.

2. The bone screw according claim 1 wherein said first thread is self-tapping at its end adjacent said intermediate section, and wherein second thread is self-tapping at said distal end.

3. The bone screw according to claim 1 wherein said first thread has a major diameter larger than said predetermined diameter and a minor diameter smaller than said predetermined diameter.

4. The bone screw according to claim 1 wherein said distal section is axially longer than said intermediate section.

5. The bone screw according to claim 1 further comprising a central longitudinal guide bore extending the entire length of said bone screw between said distal and proximal ends, and wherein said proximal end has two longitudinal recesses defined therein on diametrically opposite sides of said guide bore for receiving respective drive pins of a screwdriver.

6. The bone screw according to claim 1 wherein said first and second thread each have a compressive force-applying surface facing said intermediate section and an opposite surface, said compressive force-applying surface defining a first angle within approximately 5° of perpendicular to the length dimension of said screw, said opposite surface defining a significantly greater second angle with said length dimension.

7. The bone screw according to claim 1 wherein said first thread is self-tapping at its end adjacent said intermediate section, and wherein said second thread is self-tapping at said distal end; and
   wherein said distal section is axially longer than said intermediate section.

8. The bone screw according to claim 1 wherein said first thread has a major diameter larger than said predetermined diameter and a minor diameter smaller than said predetermined diameter; and
   wherein said second thread has a major diameter substantially equal to said predetermined diameter.

9. A bone screw for connecting two pieces of bone comprising;
   a distal end;
   a proximal end;
   a generally cylindrical unthreaded intermediate section having a predetermined diameter;
   a threaded proximal section extending from said proximal end to said intermediate section and having a first uniformly-pitched thread;
   a threaded distal section extending from said distal end to said intermediate section and having a second uniformly-pitched thread that is threaded in the same direction as said first thread;
   wherein the pitch of said second thread is greater than the pitch of said first thread; and
   wherein said threaded distal section is axially longer than said intermediate section.

10. The bone screw according to claim 9 wherein said first thread is self-tapping at its end adjacent said intermediate section, and wherein said second thread is self-tapping at said distal end.

11. The bone screw according to claim 9 wherein said first thread has a major diameter larger than said predetermined diameter and a minor diameter smaller than said predetermined diameter.

12. The bone screw according to claim 9 wherein said second thread has a major diameter substantially equal to said predetermined diameter.

13. The bone screw according to claim 9 wherein said second thread has a major diameter substantially equal to said predetermined diameter; and
   wherein said first thread is self-tapping at its end adjacent said intermediate section, and said second thread is self-tapping at said distal end.

14. The bone screw according to claim 9 further comprising a central longitudinal guide bore extending the entire length of said bone screw between said distal and proximal ends, and wherein said proximal end has two longitudinal recesses defined therein on diametrically opposite sides of said guide bore for receiving respective drive pin of a screwdriver.

15. A bone screw for connecting two pieces of bone comprising:
   a distal end;
   a proximal end;
   a generally cylindrical unthreaded intermediate section having a predetermined diameter;
   a threaded proximal section extending from said proximal end to said intermediate section and having a first uniformly-pitched thread;
   a threaded distal section extending from said distal end to said intermediate section and having a second uniformly-pitched thread that is threaded in the same direction as said first thread;

wherein the pitch of said second thread is greater than the pitch of said first thread;

wherein said first thread is self-tapping at its end adjacent said intermediate section and said second thread is self-tapping at said distal end; and wherein said first thread has a major diameter larger than said predetermined diameter and a minor diameter smaller than said predetermined diameter.

16. The bone screw according to claim 15 wherein said second thread has a major diameter substantially equal to predetermined diameter.

17. The bone screw according to claim 15 wherein said distal section is axially longer than said intermediate section.

18. The bone screw according to claim 15 wherein the major diameter of said first thread is the largest lateral dimension of said bone screw.

* * * * *